United States Patent
Kashiwazaki et al.

(10) Patent No.: US 8,804,125 B2
(45) Date of Patent: Aug. 12, 2014

(54) DETECTION METHOD FOR INTERMOLECULAR INTERACTION AND DETECTION DEVICE THEREOF

(75) Inventors: Osamu Kashiwazaki, Hachioji (JP); Naoki Izumiya, Hino (JP); Yuichi Atarashi, Hachioji (JP)

(73) Assignee: Konica Minolta, Inc., Tokyo (JP)

(*) Notice: Subject to any disclaimer, the term of this patent is extended or adjusted under 35 U.S.C. 154(b) by 0 days.

(21) Appl. No.: 13/583,612

(22) PCT Filed: Feb. 10, 2011

(86) PCT No.: PCT/JP2011/052838
§ 371 (c)(1),
(2), (4) Date: Sep. 7, 2012

(87) PCT Pub. No.: WO2011/111466
PCT Pub. Date: Sep. 15, 2011

(65) Prior Publication Data
US 2012/0327418 A1 Dec. 27, 2012

(30) Foreign Application Priority Data

Mar. 12, 2010 (JP) .................... 2010-055325
Mar. 12, 2010 (JP) .................... 2010-055328

(51) Int. Cl.
*G01N 21/00* (2006.01)
*G01N 21/55* (2014.01)
(52) U.S. Cl.
CPC .............. *G01N 21/553* (2013.01); *G01N 21/55* (2013.01)
USPC ........................................................ 356/445
(58) Field of Classification Search
CPC .............................. G01N 21/554; G01N 21/55
USPC ................................................. 356/445–448
See application file for complete search history.

(56) References Cited

U.S. PATENT DOCUMENTS

2003/0203502 A1* 10/2003 Zenhausern et al. .......... 436/164
2004/0070764 A1    4/2004 Fujimura et al.
2009/0079976 A1*  3/2009 Cunningham et al. ........ 356/246

FOREIGN PATENT DOCUMENTS

JP          11-223597     8/1999
JP          3786073       3/2006
(Continued)

OTHER PUBLICATIONS

Sandström, T. et al., "Visual detection of organic monomolecular films by interference colors", Applied Optics, Feb. 15, 1985, pp. 472-479, vol. 24, No. 4.

(Continued)

*Primary Examiner* — Michael P Stafira
(74) *Attorney, Agent, or Firm* — Holtz Holtz Goodman & Chick PC

(57) ABSTRACT

In order to calculate and specify a valley wavelength easily and in a short period of time, a detection device for intermolecular interaction is disclosed that is equipped with a detector provided with a ligand, a white light source that irradiates the detector with white light, a spectrometer that detects the light reflected from the detector, and a control device that controls the white-light source and the spectrometer, wherein the aforementioned control device obtains a reflection spectrum by calculating the reflectivity over a fixed wavelength interval, approximates the aforementioned reflection spectrum as a high-dimensional function, selects a wavelength interval comprising the minimum reflectivity from the aforementioned high-dimensional function, approximates the aforementioned high-dimensional function with the aforementioned wavelength interval as a quadratic function of a lower order, and obtains a solution by which the aforementioned quadratic function is differentiated with respect to the wavelength and the value thereof becomes 0.

4 Claims, 12 Drawing Sheets

(56) References Cited

FOREIGN PATENT DOCUMENTS

| JP | 2006-108305 | 4/2006 |
| JP | 2009-281792 | 12/2009 |

OTHER PUBLICATIONS

Fujimura, T. et al., "Silicon-Based Optical Thin-Film Biosensor Array for Real-time Measurements of Biomolecular Interaction", Japanese Journal of Applied Physics, 2005, pp. 2849-2853, vol. 44, No. 4B.

English-language International Search Report from the Japanese Patent Office mailed Apr. 19, 2011, for International Application No. PCT/JP2011/052838.

Chinese Office Action dated Jan. 6, 2014 (and English translation thereof) in counterpart Chinese Application No. 201180012931.8.

* cited by examiner

BEFORE THE BOMBINATION     AFTER THE COMBINATION

DETECTION METHOD FOR INTERMOLECULAR INTERACTION AND DETECTION DEVICE THEREOF

CROSS REFERENCE TO RELATED APPLICATIONS

This application is a national phase application under 35 U.S.C. 371 based on International Application No. PCT/JP2011/052838, filed Feb. 10, 2011, which claims the priority of Japanese Patent Application Nos. 2010-055328, filed Mar. 12, 2010, and 2010-055325, filed Mar. 12, 2010, the entire content of all of which is hereby incorporated by reference.

TECHNICAL FIELD

The present invention relates to a detection method for an intermolecular interaction and a detection device thereof, in particular to a detection method for an intermolecular interaction of a biomolecule, an organic molecule, or the like, and a detection device thereof.

BACKGROUND TECHNOLOGY

Heretofore, measurement of bonding such as an intermolecular interaction between biomolecules such as an antigen-antibody reaction, or an intermolecular interaction between organic molecules has, in general, been carried out using a label such as a radioactive substance, a phosphor. The labeling takes a lot of work, and, in particular, a labeling method to a protein is sometimes complicated, or the characteristics of a protein were sometimes changed due to the labeling. In recent years, as a means to detect a bonding between biomolecules or organic molecules easily and directly without using the label, the RIS (reflectometric interference spectroscopy) method utilizing the change of interference color of optical film has been known. Its basic principle is described in Patent Document 1, Non-patent Document 1, or the like.

When describing briefly the RIS method, detector 100, which is shown in FIG. 6, is used in this method. As it is shown in FIG. 6a, detector 100 has substrate 102, and optical film 104 is arranged on substrate 102. When white light is irradiated on detector 100 with these conditions, the spectral intensity of the white light itself is shown by solid line 106, and the spectral intensity of the reflected light of the white light is shown by solid line 108, as they are shown in FIG. 9. When the reflectance is determined from each of spectral intensities of the irradiated white light and its reflected light, reflection spectrum 110 shown by a solid line is obtained, as it is shown in FIG. 10.

For detecting the intermolecular interaction, ligand 120 is arranged on optical film 104, as it is shown in FIG. 6b. When ligand 120 is arranged on optical film 104, optical thickness 112 is changed and thereby the optical path length is changed, and then the interference wavelength is also changed. Namely, the peak position of the spectral intensity distribution of the reflected light is shifted, and as a result, as it is shown in FIG. 10, reflection spectrum 110 is shifted to reflection spectrum 122 (refer to the dotted line). In this situation, when a sample solution is poured on detector 100, ligand 120 of detector 100 is bonded with analyte 130 in the sample solution, as it is shown in FIG. 6c. When ligand 120 is bonded with analyte 130, optical thickness 112 is moreover changed, and then, as it is shown in FIG. 10, reflection spectrum 122 is shifted to reflection spectrum 132 (refer to the dashed-dotted line). Then, it is designed so that, by detecting the amount of change between the peak wavelength (bottom peak wavelength) of reflection spectrum 122 and the bottom peak wavelength of reflection spectrum 132, the intermolecular interaction can be detected.

When observing the transition of changes of the bottom peak wavelength over time, as it is shown in FIG. 11, a change of the bottom peak wavelength by ligand 120 can be confirmed at point of time 140, and further a change of the bottom peak wavelength by bonding between ligand 120 and analyte 130 can be confirmed.

PRIOR ARTS

Patent Document

Patent Document 1: Japanese Patent No. 3786073

Non-Patent Document

Non-Patent Document 1: Sandstrom et al, APPL. OPT., 24, 472, 1985

SUMMARY OF THE INVENTION

Problem to be Solved by the Invention

In the meantime, in the above RIfS method in which the transition of changes of the bottom peak wavelength over time is observed, since the true reflectance bottom peak wavelength often exists between wavelengths of the actually detected reflected light, it is necessary to follow the transition of the bottom peak wavelength over time with a smaller (narrower) wavelength interval than a wavelength interval of the actually detected reflected light. To this, it is usually performed that the wavelength distribution of reflectance is approximated by a high-degree polynomial to determine the solution (minimum value) from the high-degree polynomial, and then the solution is assigned to the bottom peak wavelength.

However, though the approximation by the high-degree polynomial is useful in terms of fitting, it takes a long time to determine a solution from the polynomial due to its high-degree, and it is difficult to calculate and specify the bottom peak wavelength easily and in a short time.

Further, the above RIfS method, in which the transition of changes of the bottom peak wavelength over time is observed, is made possible to deal with a plurality kinds of molecules, and then the intermolecular interaction can be detected even if a plurality kinds of molecules are piled together, or a sample solution is laced with a plurality kinds of analytes 130. For example, as it is shown in FIG. 12, the intermolecular interaction of proteins such as a complex antigen-antibody reaction can be detected. According to the example of FIG. 12, the detection can be performed in the following steps: the surface of optical film 104 is aminated (refer to (a)), biotin 150 is bonded through NHS-PEG4 (refer to (b)), avidin 152 is bonded (refer to (c)), antibody 156 is bonded after blocking with BSA 154, and antigen 158 is detected (refer to (e)). When observing the transition of changes of the bottom peak wavelength over time, there can be detected each of the bonding of biotin 150 and avidin 152 at interval 160, the blocking by BSA 154 at interval 162, the bonding of antibody 156 at interval 164, and the bonding of antigen 158 at interval 166 according to the concentration, as it is shown in FIG. 13.

When the bottom peak wavelengths are calculated and specified in the case where intermolecular interactions between a plurality kinds of molecules are practically detected, for example, reflection spectrum 170, such as shown in FIGS. 14a and 14b, is obtained, which spectrum is then approximated by a high-dimensional function, to calculate and specify the bottom peal wavelengths.

However, in this case, because of dealing with a plurality kinds of molecules, minimum value 172 exists in reflection spectrum 170, and then, when reflection spectrum 170 is approximated, reflection spectrum 174 affected by minimum value 172 is obtained, and the bottom peak wavelength is shifted with it. Therefore, the correct bottom peak wavelength in reflection spectrum 170 cannot sometimes be calculated and specified.

Therefore, the main purpose of the present invention is to provide a detection method for an intermolecular interaction and a detection device thereof, by which the bottom peak wavelength can be calculated and specified easily and in a short time with or without the minimum value of the reflection spectrum.

Means to Solve the Problems

According to one embodiment of the present invention, a detection method for an intermolecular interaction is provided, wherein the method is provided with a step of calculating a reflectance over a fixed wavelength interval to obtain a reflectance spectrum; a step of approximating the above reflectance spectrum by a high-dimensional function; a step of selecting a wavelength interval having the minimum reflectance from the above high-dimensional function; a step of approximating, in the above wavelength interval, the above high-dimensional function by a quadratic function, which is lower order than the high-dimensional function; and a step of differentiating the above quadratic function with respect to the wavelength to obtain a solution in which the value thereof becomes zero.

According to another embodiment of the present invention, a detection method for an intermolecular interaction is provided, wherein the method is provided with a step of calculating a reflectance at a fixed wavelength interval to obtain a reflectance spectrum; a step of filtering the above reflectance spectrum; a step of selecting, from the above reflectance spectrum after being filtered, a first wavelength interval which has the minimum reflectance, and in which an inflection point is made a boundary; a step of approximating, in the above first wavelength interval, the above reflectance spectrum after being filtered by a high-dimensional function; a step of selecting a second wavelength interval having the minimum reflectance from the above high-dimensional function; a step of approximating, in the above second wavelength interval, the above high-dimensional function by a quadratic function, which is lower order than the high-dimensional function; and a step of differentiating the above quadratic function with respect to the wavelength to obtain a solution in which the value thereof becomes zero.

According to another embodiment of the present invention, a detection device for an intermolecular interaction is provided, wherein the device is equipped with a detector provided with a ligand; a white light source which irradiates white light on the above detector; a spectrometer which detects reflected light from the above detector; and a control device, which controls the above white light source and the above spectrometer, and calculates reflectance over a fixed wavelength interval to obtain a reflectance spectrum, approximates the above reflectance spectrum by a high-dimensional function, selects a wavelength interval having the minimum reflectance from the above high-dimensional function, approximates, in the above wavelength interval, the above high-dimensional function by a quadratic function, which is lower order than the high-dimensional function, and differentiates the above quadratic function with respect to the wavelength to obtain a solution in which the value thereof becomes zero.

According to another embodiment of the present invention, a detection device for an intermolecular interaction is provided, wherein the device is equipped with a detector provided with a ligand; a white light source which irradiates white light on the above detector; a spectrometer which detects reflected light from the above detector; and a control device, which controls the above white light source and the above spectrometer, and calculates reflectance at a fixed wavelength interval to obtain reflectance spectrum, filters the above reflectance spectrum, selects, from the above reflectance spectrum after being filtered, a first wavelength interval which has the minimum reflectance, and in which an inflection point is made a boundary, approximates, in the above first wavelength interval, the above reflectance spectrum after being filtered by a high-dimensional function, selects a second wavelength interval having the minimum reflectance from the above high-dimensional function, approximates, in the above second wavelength interval, the above high-dimensional function by a quadratic function, which is lower order than the high-dimensional function, and differentiates the above quadratic function with respect to the wavelength to obtain a solution in which the value thereof becomes zero.

Effects of the Invention

According to the present invention, since, after approximating a wavelength distribution (reflection spectrum) of reflectance by a high-dimensional function, a wavelength interval is selected and the reflection spectrum is again approximated at the above wavelength interval by a quadratic function, a bottom peak wavelength can be determined by simple processing such that the above quadratic function is differentiated to obtain a solution in which the value thereof becomes zero, and the bottom peak wavelength can be calculated and specified easily and in a short time with or without a minimum value of the reflection spectrum.

MODE FOR CARRYING OUT THE INVENTION

First Embodiment

Hereinafter, a preferable first embodiment of the present invention will be described with reference to drawings.

Figure 1:
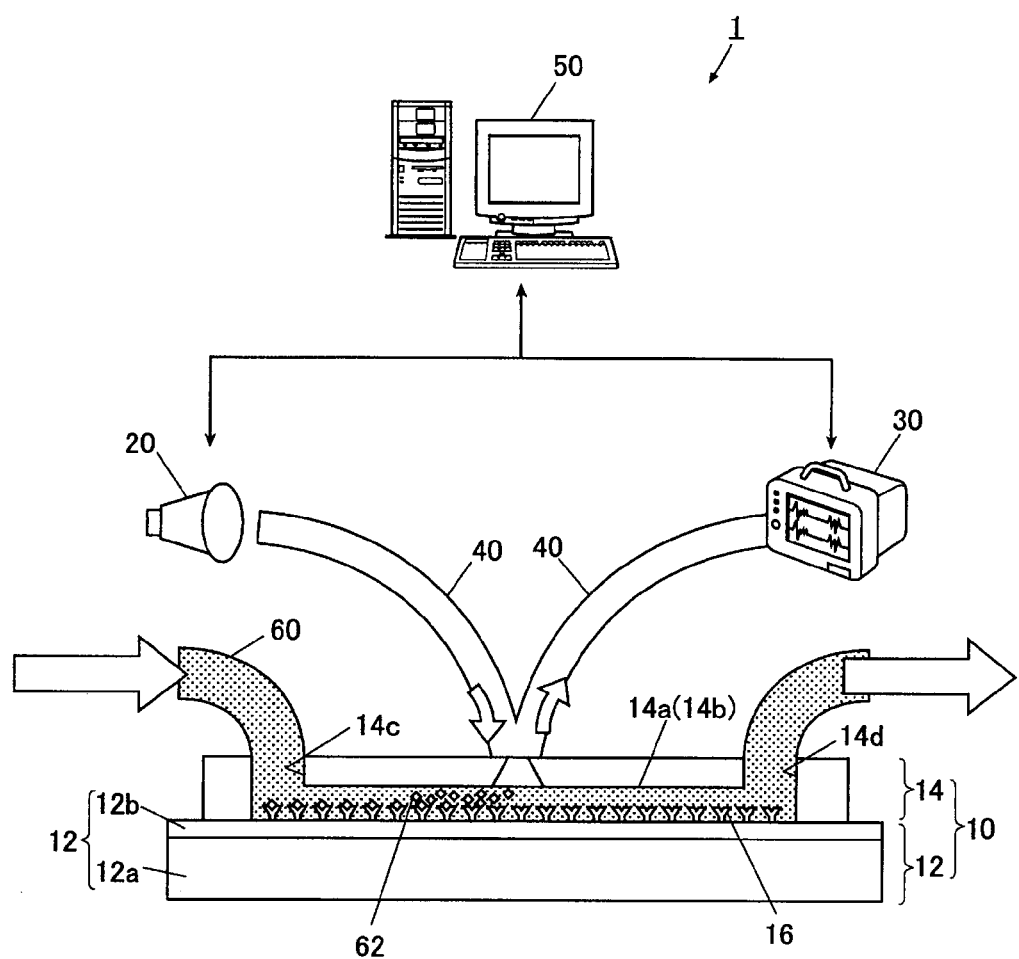
FIG. 1 is a drawing showing a schematic configuration of a detection device of an intermolecular interaction.

As it is shown in FIG. 1, detection device 1 is primarily comprised of detector 10, white light source 20, spectrometer 30, optical fiber 40, control device 50, and the like.

Detector 10 is basically comprised of sensor chip 12, and flow cell 14.

Figure 2:
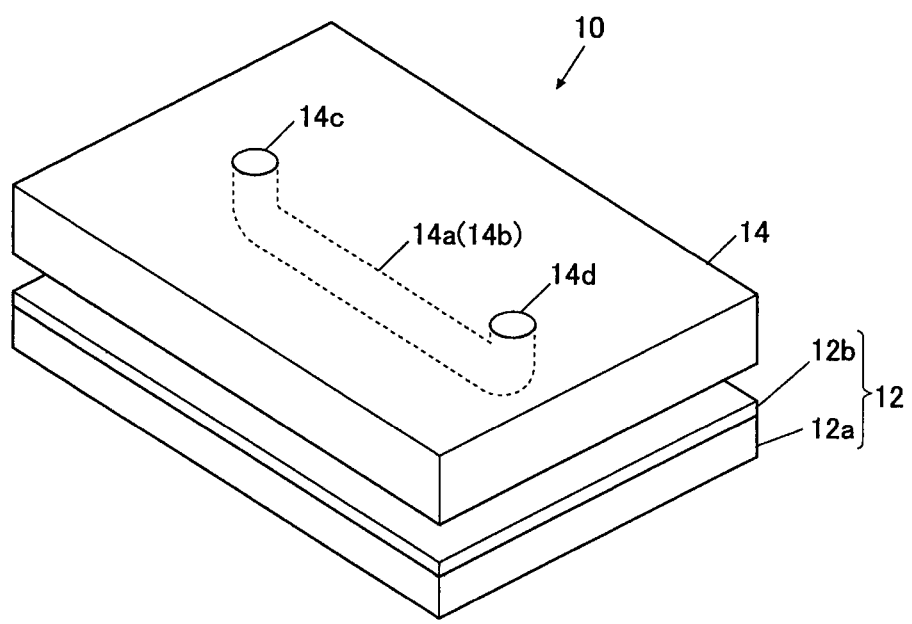
FIG. 2 is a drawing showing a schematic configuration of a detector.

As it is shown in FIG. 2, sensor chip 12 has silicon substrate 12a in a rectangular form. On silicon substrate 12a, SiN film 12b (silicon nitride) is vapor-deposited. SiN film 12b is an example of an optical film.

Flow cell 14 is a transparent member made of silicon rubber. Groove 14a is formed on flow cell 14. When flow cell 14 is made close contact with sensor chip 12, closed channel 14b is formed (refer to FIG. 1). The both ends of groove 14a are exposed from the surface of flow cell 14, and it is configured so that one end and the other end of groove 14a are functioned as inflow orifice 14c and outflow orifice 14d of a sample solution, respectively. Ligand 16 is bonded with the bottom of groove 14 (refer to FIG. 1).

In detector 10, flow cell 14 is designed to be reattachable to sensor chip 12, and flow cell 14 is made disposable. On the surface of sensor chip 12, surface modification may be carried out using a silane coupling agent or the like, and in this case, flow cell 14 is easily reattachable to the surface.

As it is shown in FIG. 1, on the upper side of closed channel 14b of flow cell 14, optical fibers 40 are arranged. With the one end of optical fiber 40, white light source 20 is connected. As white light source 20, a halogen light source is, for example, used. With the other end of optical fiber 40, spectrometer 30 is connected. If white light source 20 is turned on, the light is illuminated on closed channel 14b through optical fiber 40, and then, reflected light thereof is detected by spectrometer 30 through optical fiber 40 again. White light source 20 and spectrometer 30 are connected with control device 50, and control device 50 is designed to control actions of these members. Especially, in detection device 1, it is made so that, from the detection results by spectrometer 30, the optical characteristics or the reflection characteristics can be analyzed by control device 50.

Subsequently, the detection method for the intermolecular interaction using detection device 1 will be described.

As it is shown in FIG. 1, sample solution containing analyte 62 is passed through closed channel 14b from inflow orifice 14c to outflow orifice 14d. Analyte 62 is a substance to specifically combine with ligand 16, and is a target molecule to be detected. As analyte 62, there are used a biomolecule such as, for example, a protein, a nucleic acid, a lipid, and a sugar, a foreign substance such as a medical agent and an endocrine-disrupting chemical, which combine with the biomolecule, or the like.

While sample solution 60 is being passed through closed channel 14b, white light source 20 is turned on. The white light penetrates flow cell 14 and is irradiated on sensor chip 12, and then, the reflected light is detected by spectrometer 30. The detection intensity of the reflected light, which was detected by spectrometer 30, is transmitted to control device 50.

Figure 3:
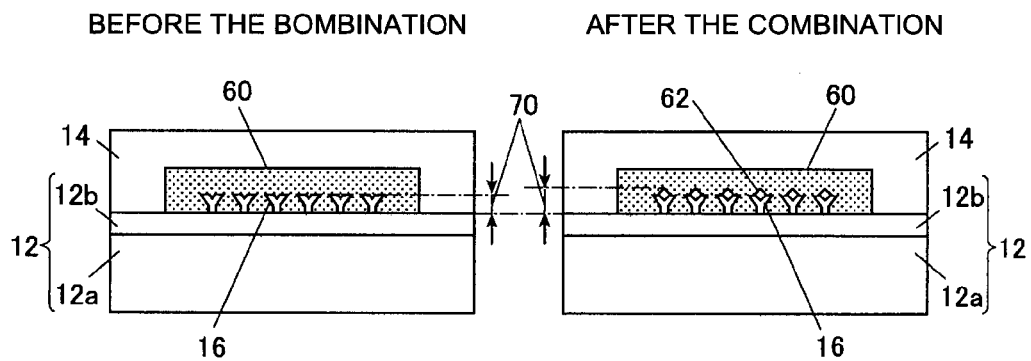
FIG. 3 is a schematic drawing showing a bonding between a ligand and an analyte.

In this case, as it is shown in FIG. 3, when analyte 62 in sample solution 60 combines with ligand 61, optical thickness 70 changes, and thereby an interference color (a wavelength in which detection intensity by spectrometer 30 becomes lowest) changes. Control device 50, after receiving the detection results by spectrometer 30, calculates and specifies each of bottom peak wavelengths $\lambda_{bottom}$ of reflection spectra before and after a combination between analyte 62 and ligand 16.

Figure 4:
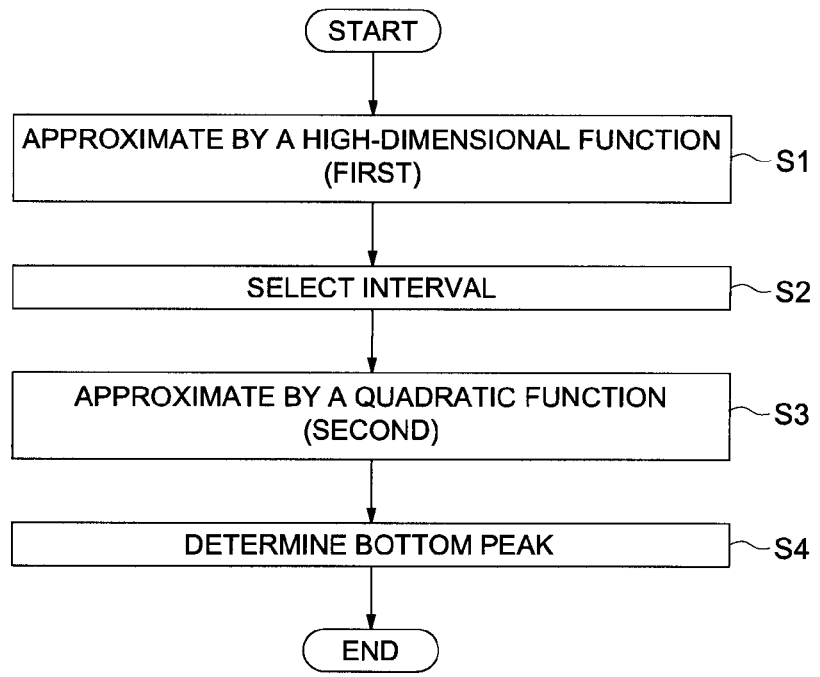
FIG. 4 is a flowchart schematically showing processing steps of a detection method for intermolecular interaction.

The method for calculating and specifying bottom peak wavelength. $\lambda_{bottom}$ is mainly comprised of steps (S1) to (S4) of FIG. 4, and the processing of steps (S1) to (S4) are carried out by control device 50.

S1: Determine a reflection spectrum and approximate it by a high-dimensional function.

S2: Select an optional wavelength interval from the high-dimensional function.

S3: Approximate, in the above wavelength interval, the above high-dimensional function by a quadratic function, which is lower order than the high-dimensional function.

S4: Determine bottom peak wavelengths $\lambda_{bottom}$ from the quadratic function.

The method for calculating and specifying bottom peak wavelength $\lambda_{bottom}$ before the bonding between analyte 62 and ligand 16 is similar to that after the bonding.

Figure 5A:
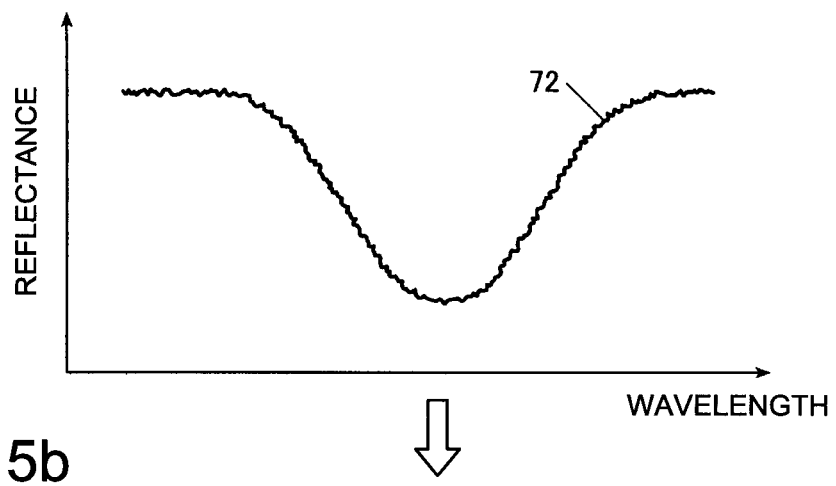
FIG. 5 includes schematic drawings describing a waveform processing in the processing steps of FIG. 4.

In step S1, from the detection results of spectrometer 30, the reflectance with respect to wavelength is calculated over a constant wavelength interval (for example, at an interval of 0.35 nm), and then, as it is shown in FIG. 5a, a relationship between the wavelength and the reflectance (reflection spectrum 72) is determined in the measured wavelength range (for example, 400 to 800 nm). At this step, the waveform of reflection spectrum 72 has an irregular form like a repetition of minute concave and convex, and therefore it is difficult to calculate and specify bottom peak wavelength $\lambda_{bottom}$.

Figure 5B:
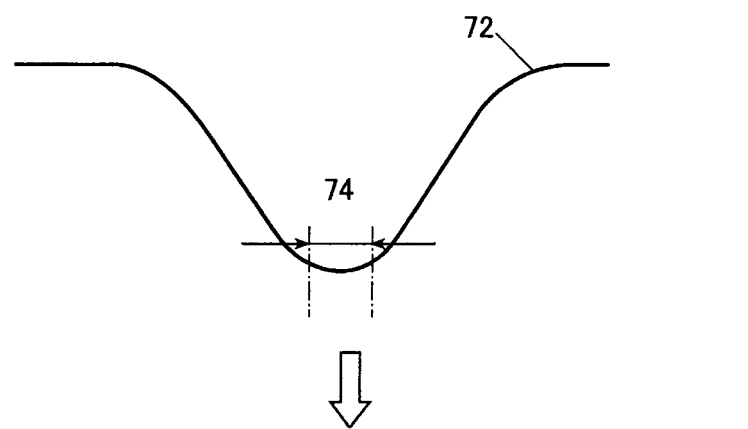

After that, reflection spectrum 72 is approximated by a high-dimensional function of about $20^{th}$ order to smooth the waveform of reflection spectrum 72 as it is shown in FIG. 5b. The aforesaid approximation may be performed by any commonly known method, and can be achieved by, for example, the sum of a linear function and the pseudo-Voigt function.

In step S2, as it is shown in FIG. 5b, in reflection spectrum 72 after the approximation (a high-dimensional function), wavelength interval 74 is optionally selected and determined with the wavelength having a minimum reflectance being taken as "standard wavelength $\lambda_0$."

Figure 5C:
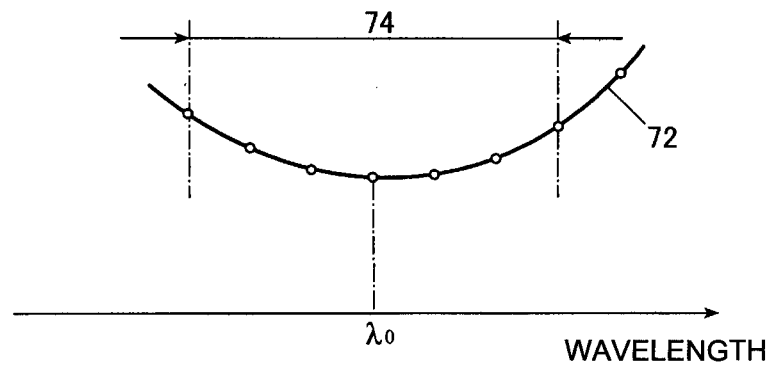
Figures 6A, 6B, 6C:
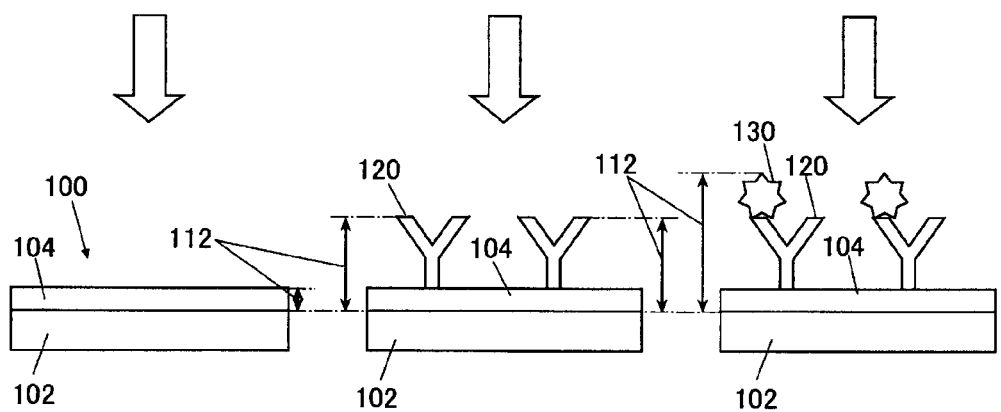
FIG. 6 includes drawings describing an outline of the RIfS method.

Namely, since, in step S1, the reflectances corresponding to the measured wavelengths have been calculated even in the high-dimensional function, the minimum wavelength is specified from these reflectances, which is then taken as standard wavelength $\lambda_0$ (refer to FIG. 5c). After that, several wavelengths are selected around standard wavelength $\lambda_0$ as the center, and the selected interval is referred to as wavelength interval 74. The selection of wavelength interval 74 is optional, and it is only necessary to select at least three wavelengths including standard wavelength $\lambda_0$.

In step S3, in wavelength interval 74, reflection spectrum 72 after the approximation (a high-dimensional function) is approximated by a quadratic function. The aforesaid approximation may be performed by any commonly known method, and can be achieved by, for example, the least square method.

In this case, the reflectance of a wavelength in wavelength interval 74 is expressed by Equation (1), where x and y indicate wavelength and reflectance, respectively.

$$y = ax^2 + bx + c \quad \text{Equation (1)}$$

In Equation (1), a, b, and c are arbitrary constants.

In step S4, bottom peak wavelength $\lambda_{bottom}$ is determined from the quadratic function expressed by Equation (1). The quadratic function expressed by Equation (1) describes a parabola that is convex downward, and if a gradient at a certain wavelength is zero, the wavelength is the one which takes the minimum reflectance and corresponds to bottom peak wavelength $\lambda_{bottom}$. Therefore, in step S4, the quadratic function expressed by Equation (1) is differentiated with respect to wavelength (x), to derive an equation in which a value after the differentiation becomes zero, and the solution is determined. The equation in which a value after the differentiation becomes zero is expressed by Equation (2), and the solution is expressed by Equation (3).

$$2ax + b = 0 \quad \text{Equation (2)}$$

$$x = -b/2a \quad \text{Equation (3)}$$

Through such processing, bottom peak wavelength $\lambda_{bottom}$ can be calculated and specified as "$-b/2a$."

According to the above-described first embodiment, reflection spectrum 72 is approximated by a high-dimensional function from the detection results of spectrometer 30 in step S1, after which wavelength interval 74 is determined in steps S2 and S3, and then reflection spectrum 72 is approximated again by a quadratic function. Therefore, by carrying out simple processing such that above quadratic function is differentiated at step S4 to obtain a solution in which the differentiated value becomes zero, bottom peak wavelength $\lambda_{bottom}$ is calculated and specified, and therefore bottom peak wavelength $\lambda_{bottom}$ can be calculated and specified easily and in a short period of time.

Second Embodiment

Hereinafter, a preferable second embodiment of the present invention will be described with reference to drawings.

The structure of the detection device in the second embodiment is the same as detection device 1 of the first embodiment.

The second embodiment differs from the first embodiment in a point of a method for calculating and specifying bottom peak wavelength $\lambda_{bottom}$. Hereinafter, a method for calculating and specifying bottom peak wavelength $\lambda_{bottom}$ in the second embodiment will be described.

Figure 7:
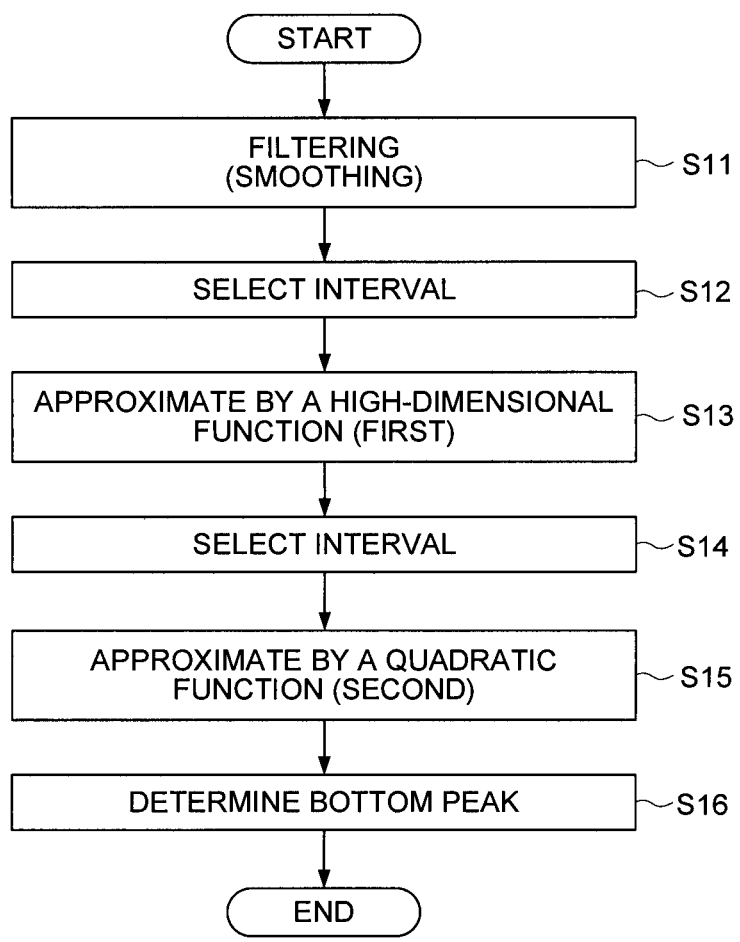
FIG. 7 is a flowchart schematically showing processing steps of a detection method for intermolecular interaction.

The method for calculating and specifying bottom peak wavelength $\lambda_{bottom}$ is mainly comprised of steps (S11) to (S16) of FIG. 7, and the processing of steps (S11) to (S16) are carried out by control device 50.

S11: Determine a reflection spectrum, which is then filtered.

S12: Select an optional wavelength interval from the reflection spectrum after the filtering.

S13: Approximate the reflection spectrum after the filtering by a high-dimensional function in the selected wavelength interval.

S14: Select an optional wavelength interval from the high-dimensional function.

S15: Approximate the above high-dimensional function by a quadratic function, which is lower order than the high-dimensional function, in the above wavelength interval.

S16: Determine bottom peak wavelengths $\lambda_{bottom}$ from the quadratic function.

The method for calculating and specifying bottom peak wavelength $\lambda_{bottom}$ before the bonding between analyte 62 and ligand 16 is similar to that after the bonding.

Figure 8A:
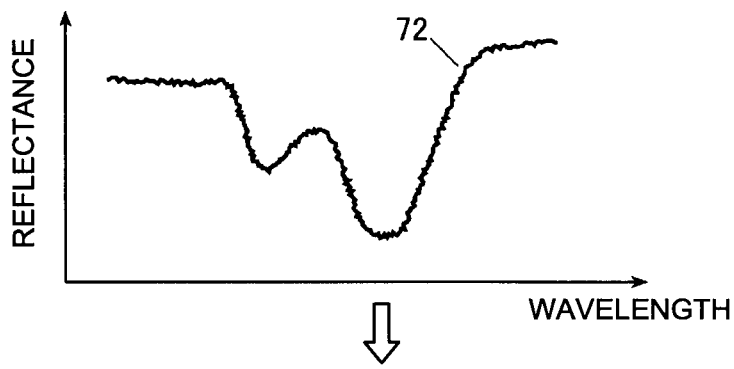
FIG. 8 includes schematic drawings describing a waveform processing in the processing steps of FIG. 7.

In step S11, from the detection results of spectrometer 30, the reflectance with respect to wavelength is calculated over a constant wavelength interval (for example, at an interval of 0.35 nm), and then, as it is shown in FIG. 8a, a relationship between the wavelength and the reflectance (reflection spectrum 72) is determined in the measured wavelength range (for example, 400 to 800 nm). At this step, the waveform of reflection spectrum 72 has an irregular form like a repetition of minute concave and convex, and therefore it is difficult to calculate and specify bottom peak wavelength $\lambda_{bottom}$.

Figure 8B:
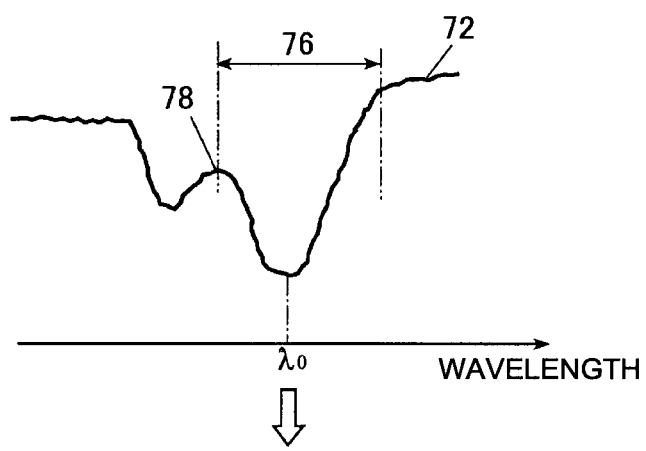

After that, reflection spectrum 72 is subjected to filtering (smoothing processing) to smooth the waveform of reflection spectrum 72 as it is shown in FIG. 8b. In the aforesaid filtering, reflectance at each wavelength is averaged at a constant wavelength interval.

In step S12, as it is shown in FIG. 8b, in reflection spectrum 72 after the filtering, wavelength interval 76 is optionally selected and determined with the wavelength having a minimum reflectance being taken as "standard wavelength $\lambda_0$."

Namely, since, in step S11, the reflectances, which are averaged at a constant wavelength interval, have been calculated, the minimum wavelength is specified from these reflectances, which is then taken as standard wavelength $\lambda_0$. After that, several wavelengths are selected around standard wavelength $\lambda_0$ as the center, and the selected interval is referred to as wavelength interval 76. In the case where inflection point 78 exists at the shorter or longer wavelength side with respect to standard wavelength 4, inflection point 78 is set as a boundary of wavelength interval 76. A point, which is away from standard wavelength $\lambda_0$ by wavelengths equivalent to several points (2 to 3 points) from inflexion point 78, may be set as a boundary of wavelength interval 76.

Figure 8C:
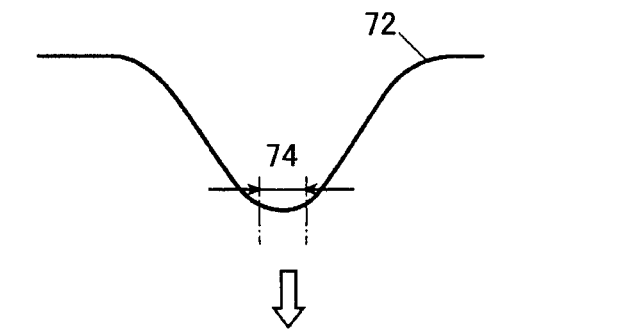

In step S13, in wavelength interval 76, reflection spectrum 72 after the filtering is approximated by a high-dimensional function of about $20^{th}$ order to further smooth the waveform of reflection spectrum 72 as it is shown in FIG. 8c. The aforesaid approximation may be performed by any commonly known method, and can be achieved by, for example, the sum of a linear function and the pseudo-Voigt function.

Figure 8D:
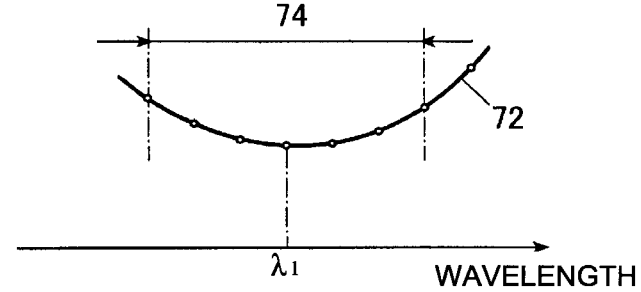
Figure 9:
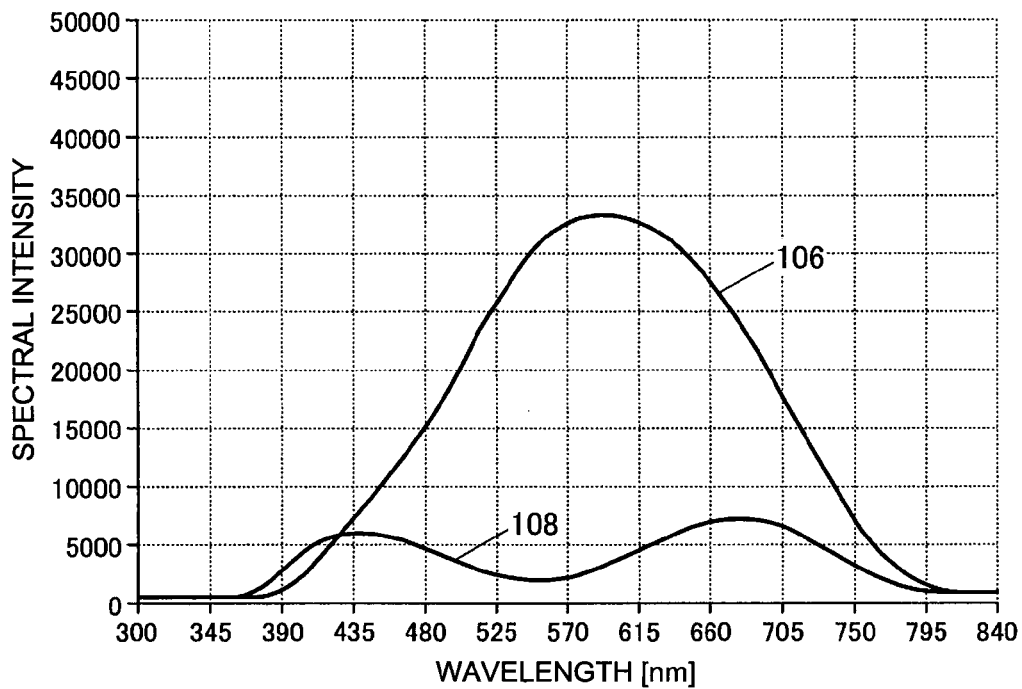
FIG. 9 is a schematic example of spectra showing a relationship between wavelength and spectral intensity.
Figure 10:
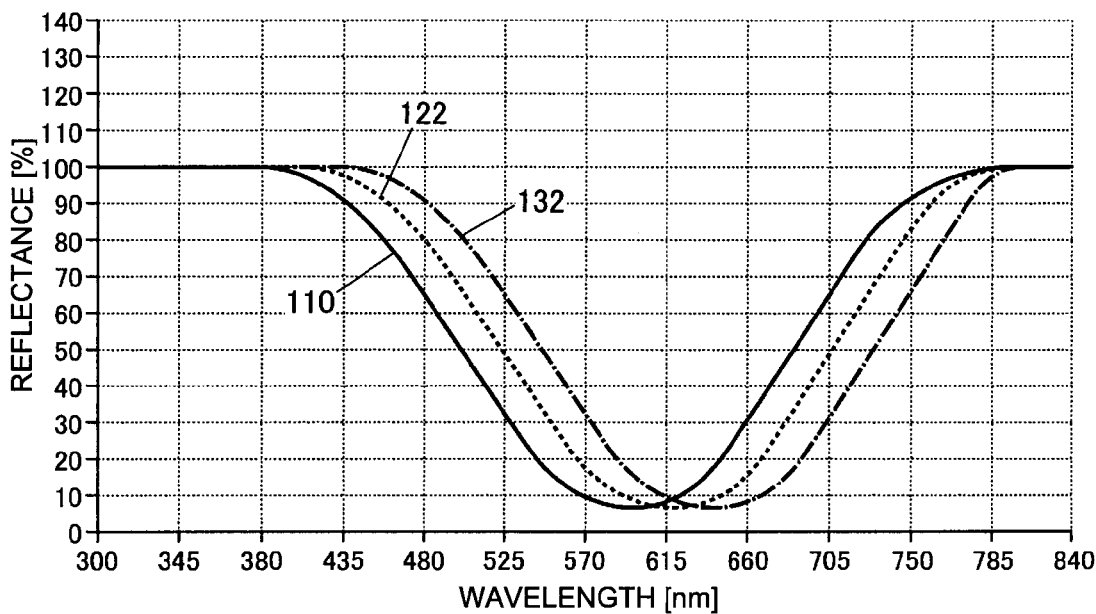
FIG. 10 is a schematic example of spectra showing a relationship between wavelength and reflectance.
Figure 11:
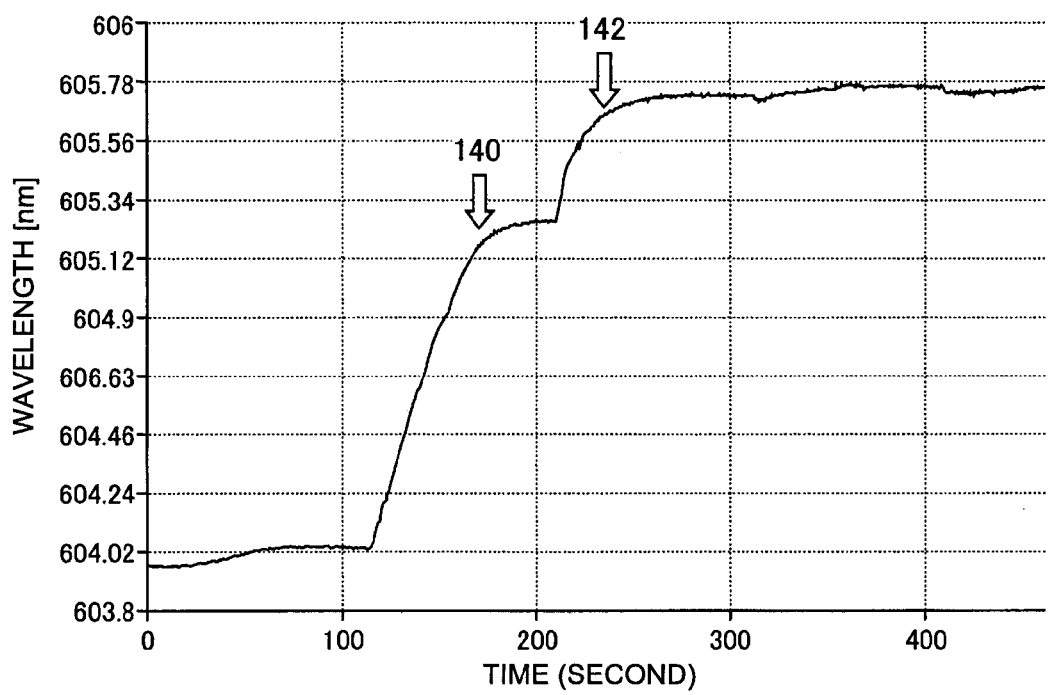
FIG. 11 is a schematic graph showing transition of changes of a bottom peak wavelength over time.
Figure 12:
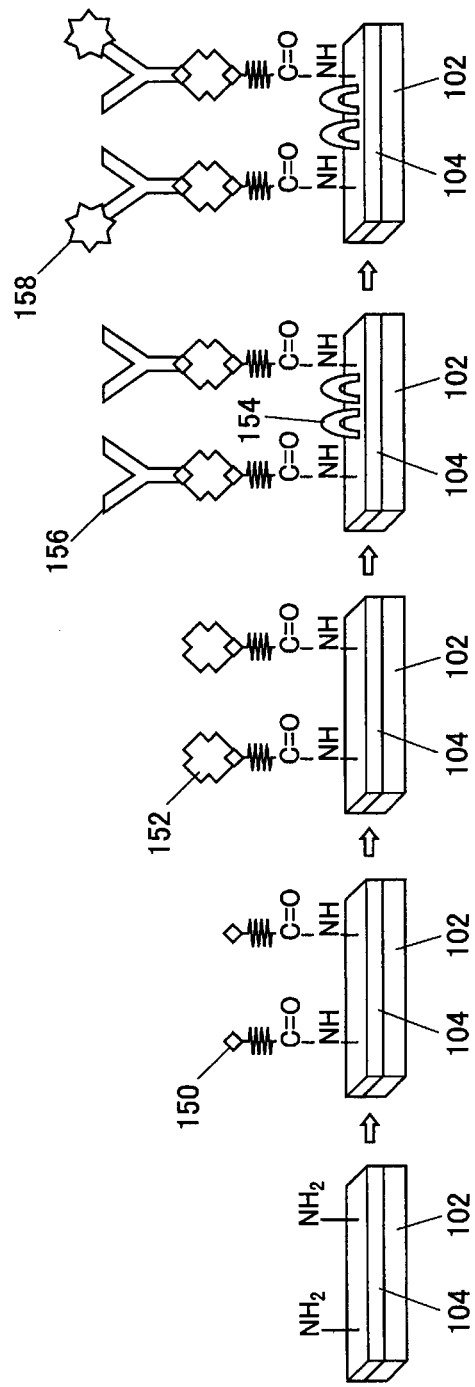
FIG. 12 includes drawings describing an example of an antigen-antibody reaction.
Figure 13:
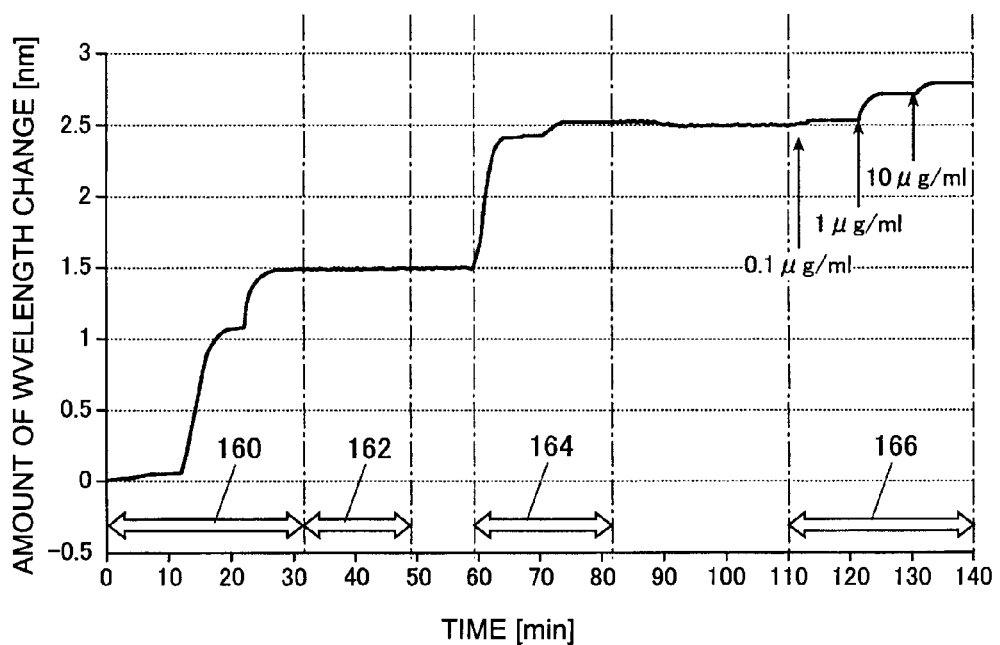
FIG. 13 is a schematic graph showing transition of changes of a bottom peak wavelength over time in the example of FIG. 12.
Figure 14A:
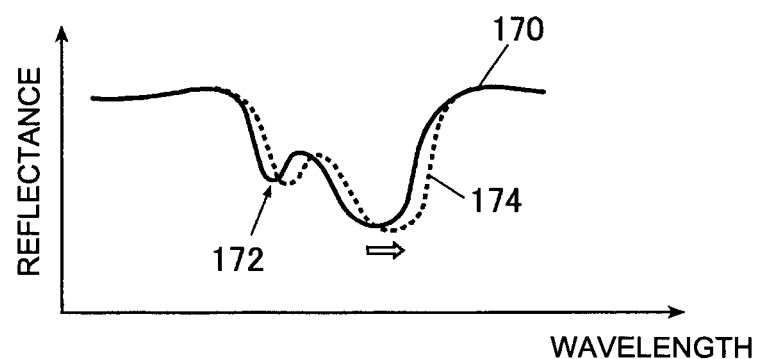
FIG. 14 includes drawings describing problems when calculating and specifying the bottom peak wavelength from a reflection spectrum.
Figure 14B:
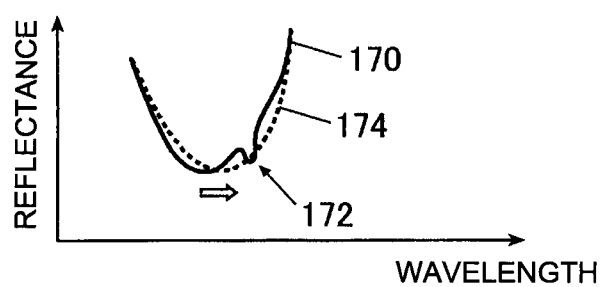

In step S14, as it is shown in FIGS. 8c, and 8d, in reflection spectrum 72 after the approximation (a high-dimensional function), wavelength interval 74 is optionally selected and determined with the wavelength having a minimum reflectance being taken as "standard wavelength $\lambda_1$."

Namely, since, in step S13, even in the high-dimensional function, the reflectances corresponding to the measured wavelengths have been calculated, the minimum wavelength is specified from these reflectances, which is then taken as standard wavelength $\lambda_1$ (refer to FIG. 8d). After that several wavelengths are selected around standard wavelength $\lambda_1$ as the center, and the selected interval is referred to as wavelength interval 74. The selection of wavelength interval 74 is optional, and it is only necessary to select at least three wavelengths including standard wavelength $\lambda_1$.

In step S15, in wavelength interval 74, reflection spectrum 72 after the approximation (a high-dimensional function) is approximated by a quadratic function. The aforesaid approximation may be performed by any commonly known method, and can be achieved by, for example, the least square method.

In this case, the reflectance of a wavelength in wavelength interval 74 is expressed by above-described Equation (1), where x and y indicate wavelength and reflectance, respectively.

In step S16, bottom peak wavelength $\lambda_{bottom}$ is determined from the quadratic function expressed by Equation (1). The quadratic function expressed by Equation (1) describes a parabola that is convex downward, and if a gradient at a certain wavelength is zero, the wavelength is the one which takes the minimum reflectance and corresponds to bottom peak wavelength $\lambda_{bottom}$. Therefore, in step S16, the quadratic function expressed by Equation (1) is differentiated with respect to wavelength (x), to derive an equation in which a value after the differentiation becomes zero, and the solution is determined. The equation in which a value after the differentiation becomes zero is expressed by above-described Equation (2), and the solution is expressed by above-described Equation (3).

Through such processing, bottom peak wavelength $\lambda_{bottom}$ can be calculated and specified as "−b/2a."

According to the above-described second embodiment, reflection spectrum 72 is subjected to the filtering to obtain reflection spectrum 72 from the detection results of spectrometer 30 in step S11, after which, in step S12, wavelength interval 76, in which inflection point 78 is taken as a boundary, is selected and determined. Therefore, even in the case where there are a plurality of minimum values in reflection spectrum 72, bottom peak wavelength $\lambda_{bottom}$ can be determined in a range in which the minimum value is avoided (a range excepting the minimum value), and then bottom peak wavelength $\lambda_{bottom}$ can be correctly calculated and specified.

Further, according to the second embodiment, in step S13, reflection spectrum 72 after the filtering is approximated by a high-dimensional function, after which wavelength interval 74 is determined in steps S14 and S15, and then reflection spectrum 72 is approximated again by a quadratic function. Therefore, by carrying out simple processing such that above quadratic function is differentiated at step S16 to obtain a solution in which the differentiated value becomes zero, bottom peak wavelength $\lambda_{bottom}$ is calculated and specified, and therefore bottom peak wavelength $\lambda_{bottom}$ can be calculated and specified easily and in a short period of time.

DESCRIPTION OF ALPHANUMERIC DESIGNATIONS

1: a detection device
10: a detector
12: a sensor chip
12a: a silicon substrate
12b: an SiN film
14: a flow cell
14a: a groove
14b: a closed channel
14c: an inflow orifice
14d: an outflow orifice
16: a ligand
20: a white light source
30: a spectrometer
40: an optical fiber
50: a control device
60: a sample solution
62: an analyte
70: an optical thickness
72: a reflection spectrum
74: a wavelength interval
100: a detector
102: a substrate
104: an optical film
106 and 108: a solid line
110: a reflection spectrum
112: an optical thickness
120: a ligand
122: a reflection spectrum
130: an analyte
132: a reflection spectrum
140 and 142: a point of time
150: a biotin
152: an avidin
154: a BSA
156: an antibody
158: an antigen
160, 162, 164, and 166: an interval
170: a reflection spectrum
172: the minimum value
174: a reflection spectrum

The invention claimed is:

1. A detection method for an intermolecular interaction comprising:
   a step of shining light on a ligand;
   a step of measuring, by a spectrometer, light reflected by the ligand;
   a step of calculating, by a control device from the reflected light, a reflectance over a fixed wavelength interval to obtain a reflectance spectrum;
   a step of approximating, by the control device, the reflectance spectrum by a high-dimensional function;
   a step of selecting, by the control device, a wavelength interval having a minimum reflectance from the high-dimensional function;
   a step of approximating, by the control device in the wavelength interval, the high-dimensional function by a quadratic function, which is lower order than the high-dimensional function;
   a step of differentiating, by the control device, the quadratic function with respect to the wavelength to obtain a solution in which a value thereof becomes zero; and
   a step of generating, by the control device from the solution, an output signal indicating a bottom peak wavelength.

2. A detection method for an intermolecular interaction comprising:
   a step of shining light on a ligand;
   a step of measuring, by a spectrometer, light reflected by the ligand,
   a step of calculating, by a control device from the reflected light, a reflectance at a fixed wavelength interval to obtain a reflectance spectrum;
   a step of filtering, by the control device, the reflectance spectrum;
   a step of selecting, by the control device from the reflectance spectrum after being filtered, a first wavelength interval which has a minimum reflectance, and in which an inflection point is made a boundary;
   a step of approximating, by the control device in the first wavelength interval, the reflectance spectrum after being filtered by a high-dimensional function;
   a step of selecting, by the control device, a second wavelength interval having the minimum reflectance from the high-dimensional function;
   a step of approximating, by the control device in the second wavelength interval, the high-dimensional function by a quadratic function, which is lower order than the high-dimensional function;

a step of differentiating, by the control device, the quadratic function with respect to the wavelength to obtain a solution in which the value thereof becomes zero; and a step of generating, by the control device from the solution, an output signal indicating a bottom peak wavelength.

3. A detection device for an intermolecular interaction comprising:

a detector provided with a ligand;
a white light source which irradiates white light on the detector;
a spectrometer which detects reflected light from the detector; and
a control device configured to:
  control the white light source and the spectrometer;
  calculate reflectance over a fixed wavelength interval to obtain a reflectance spectrum;
  approximate the reflectance spectrum by a high-dimensional function;
  select a wavelength interval having the minimum reflectance from the high-dimensional function;
  approximate, in the wavelength interval, the high-dimensional function by a quadratic function, which is lower order than the high-dimensional function;
  differentiate the quadratic function with respect to the wavelength to obtain a solution in which a value thereof becomes zero; and
  generate, from the solution, an output signal indicating a bottom peak wavelength.

4. A detection device for an intermolecular interaction comprising:

a detector provided with a ligand;
a white light source which irradiates white light on the detector;
a spectrometer which detects reflected light from the detector; and
a control device configured to:
  control the white light source and the spectrometer;
  calculate reflectance at a fixed wavelength interval to obtain reflectance spectrum;
  filter the reflectance spectrum;
  select, from the reflectance spectrum after being filtered, a first wavelength interval which has a minimum reflectance, and in which an inflection point is made a boundary;
  approximate, in the first wavelength interval, the reflectance spectrum after being filtered by a high-dimensional function;
  select a second wavelength interval having the minimum reflectance from the high-dimensional function;
  approximate, in the second wavelength interval, the high-dimensional function by a quadratic function, which is lower order than the high-dimensional function;
  differentiate the quadratic function with respect to the wavelength to obtain a solution in which the value thereof becomes zero; and
  generate, from the solution, an output signal indicating a bottom peak wavelength.

* * * * *